United States Patent

Samain

[11] Patent Number: 5,989,534
[45] Date of Patent: Nov. 23, 1999

[54] PROCESS FOR THE PERMANENT DEFORMATION OF KERATINOUS MATTER

[75] Inventor: Henri Samain, Bievres, France

[73] Assignee: L'Oreal, Paris, France

[21] Appl. No.: 08/955,283

[22] Filed: Oct. 21, 1997

Related U.S. Application Data

[63] Continuation of application No. 08/397,263, filed as application No. PCT/FR94/00832, Jul. 6, 1994.

[30] Foreign Application Priority Data

Jul. 16, 1993 [FR] France ................................ 93-08750

[51] Int. Cl.$^6$ .......................................... A61K 7/06
[52] U.S. Cl. .......................................... 424/70.51; 424/70.2
[58] Field of Search .................................. 424/70.2, 70.51

[56] References Cited

U.S. PATENT DOCUMENTS

| | | | |
|---|---|---|---|
| 4,947,878 | 8/1990 | Crews et al. | 132/203 |
| 5,101,841 | 4/1992 | Crews et al. | 132/203 |
| 5,208,014 | 5/1993 | Dubief et al. | 424/71 |
| 5,332,570 | 7/1994 | Bergstrom et al. | 424/72 |

FOREIGN PATENT DOCUMENTS

| | | |
|---|---|---|
| A-0320612 | 6/1989 | European Pat. Off. . |
| A-0432051 | 6/1991 | European Pat. Off. . |
| A-0551135 | 7/1993 | European Pat. Off. . |
| A-2683999 | 5/1993 | France . |

OTHER PUBLICATIONS

Derwent Abstract of FR–A–2683999, May 1993.
Derwent Abstract of EP–A–0320612, Jun. 1989.

*Primary Examiner*—Thurman K. Page
*Assistant Examiner*—Alysia Berman
*Attorney, Agent, or Firm*—Finnegan, Henderson, Farabow, Garrett & Dunner, L.L.P.

[57] ABSTRACT

The invention relates to a new process for the treatment of keratinous matter, in particular hair, with a view to obtaining permanent deformation of the latter, in particular in the form of permanent-waved hair, the said process being characterized in that it contains the following stages: (i) a composition containing cysteine and/or cysteamine and/or one of their salts is applied on the keratinous matter to be treated, the pH of the said composition being between 9 and 10 when the latter contains cysteine or between 8 and 9 when the latter contains cysteamine, the means (rollers) necessary for placing the keratinous matter under mechanical tension being used before, during or after the said application, (ii) the keratinous matter, thus treated, is then subjected to a heat treatment (heating) carried out at a temperature of between 30 and 60° C., (iii) the keratinous matter, thus treated, is then rinsed, (iv) the keratinous matter, thus rinsed, is then allowed to rest, (v) and, finally, the keratinous matter, thus allowed to rest, is separated from the tensioning means used in Stage (i). The process according to the invention makes it possible, among other advantages, to dispense with the use of oxidizing (fixation) agents.

17 Claims, No Drawings

PROCESS FOR THE PERMANENT DEFORMATION OF KERATINOUS MATTER

This is a continuation of application Ser. No. 08/397,263, filed May 18, 1995, now abandoned, which is a 371 of PCT/FR94/00832 filed Jul. 6, 1994.

The present invention relates to a new process for the treatment of keratinous matter, in particular of the hair, for the purpose of obtaining permanent deformation of the latter, in particular in the form of permanent-waved hair, the said process being especially useful in the field of professional hairdressing, beauty and cosmetic salons and similar.

It is known that the most usual technique for obtaining permanent hair deformation consists, in a first step, in opening the —S—S— disulphide bonds of keratin (cystine) using a composition containing a reducing agent (reduction stage) and then, preferably after having rinsed the hair which has thus been treated, in reconstituting, in a second step, the said disulphide bonds by applying an oxidizing composition (oxidation stage, also known as fixing stage) on the hair which has been placed under tension beforehand (curlers and others), so as finally to give the desired shape to the hair. This technique thus makes it possible without distinction to carry out either waving of the hair or its straightening or its decrimping. The new shape imposed on the hair by a chemical treatment such as above is eminently durable with time and is especially resistant to the effect of washing with water or with shampoos, in contrast to simple conventional techniques for non-permanent deformation, such as setting.

The reducing compositions which can be used for carrying out the first stage of a permanent wave operation generally contain, as reducing agents, sulphites, bisulphites or, preferably, thiols. Among the latter, those commonly used are cysteine and its various derivatives, cysteamine and its derivatives, thiolactic acid, thioglycolic acid and its esters, especially glyceryl monothioglycolate, and thioglycerol. In this respect, and despite having an unpleasant smell, thioglycolic acid is particularly effective and thus constitutes the reference permanent wave compound for reducing the disulphide bonds of keratin; cysteine, for its part, produces a much weaker smell than that of thioglycolic acid or of glyceryl monothioglycolate, but the degree of curliness obtained is unfortunately lower and far from being entirely satisfactory.

As regards the oxidizing compositions necessary for carrying out the fixation stage, recourse is most often had, in practice, to compositions based on hydrogen peroxide. It turns out, however, that the use of hydrogen peroxide has especially the disadvantage of leading to a more or less marked deterioration in the original colour of the hair.

In addition, and in particular in the case where the reducing agent used is thioglycolic acid, it is observed that the sequence of reduction/oxidation cycles (i.e. permanent wave operations) on the hair unfortunately leads to a progressive deterioration not only in the colour of the latter (bleaching) but also in its mechanical strength (decrease in the energy at break), due in particular to a significant increase in the level of keratocysteic acid in the treated hair.

The aim of the present invention is especially to solve the above problems.

More precisely still, the aim of the present invention is to propose a new treatment process suitable for the permanent deformation of keratinous matter and which makes it possible to dispense with the use of the conventional fixation stages with oxidizing agents.

Another aim of the present invention is to propose a process as above which additionally makes it possible to obtain high quality curlinesses.

Another aim of the present invention is to propose a process as above which makes it possible to limit, or indeed suppress, mechanical deterioration of the hair, after repetition of the treatment.

Another aim of the present invention is to propose a process as above limiting, or indeed suppressing, bleaching of the hair.

A final aim of the present invention is to propose a process as above which has, overall, little smell, on the one hand, and little irritation for the skin and/or the scalp, on the other hand.

Now, it has been found by the Applicant Company that these aims, and others, could be achieved with success by carrying out a suitable selection of the starting so-called reducing composition in combination with a specific procedure for using this composition. This discovery is the basis of the present invention.

Thus, there is now proposed, according to the present invention, a new treatment process suitable for the permanent deformation and/or shaping of keratinous matter and in particular of the hair, the said process being characterized in that it comprises the following stages:

(i) a composition containing cysteine and/or cysteamine, and/or one of their salts, is applied on the keratinous matter to be treated, the pH of the said composition being between 9 and 10 when the latter contains cysteine or between 8 and 9 when the latter contains cysteamine, the means (such as, for example, rollers, curlers and similar) necessary for placing the keratinous matter under mechanical tension being used before, during or after the said application, (ii) the keratinous matter thus treated is then subjected to a heat treatment carried out at a temperature of between 30 and 60° C., (iii) the keratinous matter thus treated is then rinsed, (iv) the keratinous matter thus rinsed is then allowed to rest for a time of between 10 and 60 min, (v) and, finally, the keratinous matter thus allowed to rest is separated from the tensioning means (rollers and others) used in Stage (i).

The process according to the invention is particularly well suited to producing permanent-waved hair.

When applied to healthy hair, and even when repeated a number of times, the process according to the invention has the main advantages, inter alia, of leading, without giving off unpleasant smells, on the one hand, and without irritating the skin and/or the scalp, on the other hand, to hair which is unbleached or substantially unbleached, which is mechanically resistant and which has beautiful curliness. This last point is all the more unexpected and surprising since the "reducing" agents, and in particular cysteine, used in the context of the present invention are reputed to give unsatisfactory curlinesses when they are used under conventional conditions for use of the processes based on the reduction/oxidation operations mentioned above.

However, other characteristics, aspects and advantages of the invention will become still more clearly apparent on reading the detailed description which will follow, as well as various concrete, but in no way limiting, examples intended to illustrate it.

Although the account which follows is essentially concerned with the specific case of hair treatment, it should be noted here that the process according to the invention is applicable to any keratinous matter in general, especially eyelashes, moustaches, hairs, wool and others.

The reducing agents used in the context of the process according to the invention are cysteine, of formula (1):

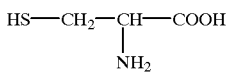

and cysteamine, of formula (2):

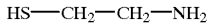

or one of their salts.

Mention may more particularly be made, among the cosmetically acceptable salts of the products (1) and (2) above, of hydrochlorides, hydrobromides, citrates, acetates and sulphates.

Preferably, cysteine is used as reducing agent.

Although the above agents are named here, purely for convenience, as "reducing" agents, it is not certain that, under the specific conditions of the process according to the invention, they effectively exert a reducing function on the keratinous matter on which they are applied (opening of the —S—S— bonds).

These reducing agents are generally used in cosmetically acceptable compositions, which are, moreover, already well known per se in the state of the existing art of curling formulations intended for carrying out the first stage (reduction) of a permanent wave operation. Thus, mention may more particularly be made, as usual and conventional additives, which can be used alone or as mixtures, of surface-active agents of non-ionic, anionic, cationic or amphoteric type and, among them, mention may be made of alkyl sulphates, alkylbenzene sulphates, alkyl ether sulphates, alkyl sulphonates, quaternary ammonium salts, alkyl betaines, oxyethylenated alkylphenols, fatty acid alkanolamides, oxyethylenated fatty acid esters and other non-ionic surface-active agents of hydroxypropyl ether type.

When the reducing composition contains at least one surface-active agent, the latter is generally present at a maximum concentration of 30% by weight, and preferably of between 0.5 and 10% by weight, with respect to the total weight of the reducing composition.

With the aim of improving the cosmetic properties of the hair or alternatively of lessening or preventing their deterioration, the reducing composition can also contain a treatment agent of cationic, anionic, non-ionic or amphoteric nature.

Mention may especially be made, among particularly preferred treatment agents, of those described in French Patent Applications No. 2,598,613 and 2,470,596. It is also possible to use, as treatment agents, volatile or nonvolatile, linear or cyclic silicones and their mixtures, polydimethylsiloxanes, quaternized polyorganosiloxanes such as those described in French Patent Application No. 2,535,730, polyorganosiloxanes containing aminoalkyl groups modified by alkoxycarbonylalkyl groups, such as those described in U.S. Pat. No. 4,749,732, polyorganosiloxanes such as the polydimethylsiloxane-polyoxyalkyl copolymer of Dimethicone Copolyol type, a polydimethylsiloxane containing end stearoxy groups (stearoxydimethicone), a polydimethylsiloxane-dialkylammonium acetate copolymer or a polydimethylsiloxane-poly(alkyl betaine) copolymer described in British Patent Application No. 2,197,352, polysiloxanes organomodified by mercapto or mercaptoalkyl groups, such as those described in French Patent No. 1,530, 369 and in European Patent Application No. 295,780, and silanes, such as stearoxytrimethylsilane.

The reducing composition can also contain other treatment ingredients such as cationic polymers, such as those used in the compositions of French Patents No. 79.32078 (FR-A-2,472,382) and 80.26421 (FR-A-2,495,931), or alternatively cationic polymers of the ionene type, such as those used in the compositions of Luxembourgian Patent No. 83703, basic amino acids (such as lysine or arginine) or acidic amino acids (such as glutamic acid or aspartic acid), peptides and their derivatives, protein hydrolysates, waxes, swelling and penetrating agents or agents which make it possible to reinforce the effectiveness of the reducing agent, such as the $SiO_2$/PDMS (polydimethylsiloxane) mixture, dimethyl isosorbitol, urea and its derivatives, pyrrolidone, N-alkylpyrrolidones, thiamorpholinone, the alkyl ethers of alkylene glycol or of dialkylene glycol, such as, for example, the monomethyl ether of propylene glycol, the monomethyl ether of dipropylene glycol, the monoethyl ether of ethylene glycol and the monoethyl ether of diethylene glycol, $C_3$–$C_6$ alkanediols, such as, for example, 1,2-propanediol and 1,2-butanediol, or 2-imidazolidinone, and other compounds such as fatty alcohols, lanolin derivatives, active ingredients such as pantothenic acid, anti-hair-loss agents, anti-dandruff agents, thickening agents, suspending agents, sequestering agents, opacifying agents, dyes, sunscreens and fragrances and preserving agents.

The pH of the reducing composition can be obtained and/or adjusted conventionally by addition either of basifying agents, such as, for example, ammonia, monoethanolamine, diethanolamine, triethanolamine, isopropanolamine, 1,3-propanediamine, an alkali metal or ammonium carbonate or bicarbonate, an organic carbonate, such as guanidinium carbonate, or alternatively an alkali metal hydroxide, it being possible, of course, for all these compounds to be taken alone or as a mixture, or acidifying agents, such as, for example, hydrochloric acid, acetic acid, lactic acid or boric acid.

In the reducing permanent-wave compositions which can be used in the context of the invention, the reducing agents mentioned above are generally present at a concentration which can be between 1 and 30% by weight, and preferably between 5 and 20% by weight, with respect to the total weight of the reducing composition.

The reducing composition can be provided in the form of a lotion, which is or is not thickened, of a cream, of a gel or in any other appropriate form.

The reducing composition can also be of the exothermic type, that is to say, causing a certain heating during application on the hair, which is pleasant to the person who is being subjected to the permanent wave or to the hair straightening.

The reducing composition can also contain a solvent, such as, for example, ethanol, propanol or isopropanol or alternatively glycerol, at a maximum concentration of 20% with respect to the total weight of the composition.

The vehicle of the compositions is preferably water or a water/alcoholic solution of a lower alcohol such as ethanol, isopropanol or butanol.

When the compositions are intended for a hair straightening or decrimping operation, the reducing composition is preferably in the form of a thickened cream, so as to keep the hair as stiff as possible. These creams are produced in the form of "heavy" emulsions, for example based on glyceryl stearate, glycol stearate, self-emulsifiable waxes, fatty alcohols, and the like.

It is also possible to use liquids or gels containing thickening agents such as carboxyvinyl polymers or copolymers which "stick" the hair and keep it in the smooth position during exposure.

Finally, the compositions can also be in the so-called "self-neutralizing" or alternatively "self-regulated" form and, in this case, the reducing agents of general formula (1) and (2) are combined with at least one disulphide known for its use in a self-neutralizing reducing composition for a permanent wave.

Mention may especially be made, among such known disulphides, of dithioglycolic acid, dithioglycerol, cystamine, N,N'-diacetylcystamine, cystine, pantethine, and the disulphides of N-(mercaptoalkyl)-ω-hydroxyalkylamides described in European Patent Application EP 354,835, the disulphides of N-mono- or N,N-dialkyl-4-mercaptobutyramides described in Patent Application EP 368,763, the disulphides of aminomercaptoalkylamides described in Patent Application EP 403,267, and the disulphides of alkylaminomercaptoalkylamides described in Patent Application EP 432,000. These disulphides are generally present in a molar ratio of 0.5 to 2.5, and preferably of 1 to 2, with respect to the reducing agent (see U.S. Pat. No. 3,768,490).

In accordance with the first stage of the process according to the present invention (Stage (i)), the compositions containing the reducing agent(s) of formulae (1) or (2) given above, or one of their salts, are then applied on the hair to be treated, which will preferably have been made wet beforehand. This application can be carried out before, during or after the usual stage of tensioning the hair in a shape corresponding to the desired final shape for the latter (curls, for example), it being possible for this stage itself to be carried out by any appropriate means, especially mechanical, known per se for maintaining hair under tension, such as, for example, rollers, curlers and similar.

After application of the reducing composition, the hair is subjected to a heat treatment, that is to say a heating. In this case, the heating temperature is generally between 30 and 60° C. This heating makes it possible to adjust the final degree of curliness of the hair as desired. In practice, this operation can be carried out by means of a hairdryer hood, a hand-held hairdryer, an infrared radiation dispenser or any other conventional heating device.

Before carrying out the following rinsing stage, it is advisable, conventionally, to allow the hair on which the reducing composition has been applied to rest for a few minutes, generally between 2 and 30 min and preferably between 5 and 20 min, so as to allow the reducing agent plenty of time to act correctly on the hair; during this waiting phase, which combines the heating stage mentioned above, care is taken that the hair does not completely dry and thus remains damp up to the time of the implementation of the following stage (possible use of caps or protective gels, for example).

In a third essential stage of the process according to the invention (Stage (iii)), the hair impregnated with reducing composition is then carefully rinsed, generally with water.

According to a fourth, absolutely essential, stage of the treatment process according to the invention (Stage (iv)), the hair, thus rinsed, is then left in a resting or waiting phase for a time of between 10 and 60 min. As the examples given below will clearly show, if this stage is suppressed, it is not possible to obtain correct curliness. According to the invention, this resting (or waiting) phase of the rinsed hair is preferably between 15 and 30 min. It is generally carried out by allowing the wet hair resulting from the rinsing to rest while exposed to the air (room temperature), but is preferably carried out at a higher temperature, in particular between 30 and 60° C. It should be noted that this stage can be carried out until entirely dry hair is obtained, the process according to the invention then, in this case, being similar (except as regards the result) to the processes known as "hair setting".

Finally, in the last stage of the process according to the invention (Stage (v)), the mechanical means (rollers, curlers and similar), which kept the hair under tension and in the desired shape throughout the treatment, are removed from the hair, whereby it is possible finally to obtain hair having, for example, good permanent-wave curls (in particular resistant to water), without the chemical fixation (oxidation) stage having to be carried out.

Except for the specific case of the process of "hair setting" type mentioned above, it should be noted that, before or after the implementation of Stage (v) above (removal of the mechanical means for tensioning the hair), it is possible to implement a new stage of rinsing the hair with water. When removal of the rollers is carried out on hair which is already entirely dry, the implementation of a new rinsing stage proves to be important if it is wished to hope to obtain good curliness.

Concrete examples illustrating the invention will now be given. For the purposes of a significant comparison, the same starting hair (before treatment) was used in all the examples.

EXAMPLE 1

Invention

A reducing composition having the following characteristics is used:

| | |
|---|---|
| cysteine | 12.2 g |
| monoethanolamine | q.s. pH 9.5 |
| demineralized water | q.s. 100 g |

The procedure is the following: the above reducing composition is applied on damp hair which is wound around rollers (diameter of the rollers: 9 mm); a plastic cap is then placed on the hair (which makes it possible to prevent drying of the hair during the following heating stage) which is then placed under an infrared dispenser (40° C.) for 15 minutes; then the cap is removed and rinsing is carried out copiously and carefully with water; the hair is then allowed to rest on the rollers for 15 minutes; the rollers are then removed (unwinding); finally, rinsing is again carried out with water.

Thus, there is finally obtained a lock No. 1 having good curliness. By measuring the mean radii of curvature of the curls obtained at mid-length, an excellent radius of curvature of 1.33 cm is recorded.

EXAMPLE 2

Comparative

The procedure is carried out as in Example 1, except for this difference: the rollers are, in this instance, removed immediately after the first rinsing.

There is then obtained a lock No. 2 having excessively weak curls, the measured mean radius of curvature of which is 6 cm.

EXAMPLE 3

Invention

The procedure of the treatment given in Example 1 is repeated six times in an identical fashion and on the same hair.

Thus, there is finally obtained a lock No. 3 having the following trichromacity coordinates L, a and b (measured on a Minolta Chromameter CR 200 colorimeter):

L=19.5; a=2.22; b=2.32

EXAMPLE 4

Comparative

The procedure is carried out as in Example 3, except for this difference: the treatment, which is repeated six times, furthermore comprises, this time, an additional fixation (oxidation) stage carried out by means of an 8 V hydrogen peroxide solution with pH 3 (acidity introduced by addition of citric acid) which is allowed to act for 5 min, this additional stage being inserted just between the first rinsing stage and the unwinding stage.

Thus, there is finally obtained a lock No. 4 having the following chromaticity coordinates (same measuring apparatus as in Example 3):

L=20.89; a=3.85; b=4.64

This lock is thus much more bleached than the lock No. 3 obtained in Example 3.

EXAMPLE 5

Invention

The procedure of the treatment given in Example 1 is repeated twice in an identical way and on the same hair.

Thus, there is finally obtained a lock No. 5 consisting of hair whose mean energy at break (over 20 measurements) is equal to $4.1 \times 10^{-3}$ J (measurement carried out hair by hair by means of an Instron 1122 extensometer; stretching rate: 100 mm/min; distance between mortises: 2 cm).

EXAMPLE 6

Comparative

The treatment which is indicated in Example 4 is repeated twice in an identical way (addition of a fixation stage by means of hydrogen peroxide).

Thus, there is finally obtained a lock No. 6 consisting of hair whose mean energy at break is equal to $3.77 \times 10^{-3}$ J (apparatus and parameters identical to those of Example 5).

This lock is therefore much less resistant than the lock No. 5 obtained in Example 5 ($\Delta E = 8\%$).

EXAMPLE 7

Invention

The procedure of the treatment given in Example 1 is repeated five times in an identical way and on the same hair.

Thus, there is finally obtained a lock No. 7 in which the level of keratocysteic acid was measured equal to 0.8% by weight, that is to say a value strictly equal to the initial level of keratocysteic acid in the starting hair (before any treatment).

EXAMPLE 8

Comparative

The following treatment is repeated five times in an identical way and on the same hair: a reducing composition containing 9.2 g of thioglycolic acid, brought to pH 8.5 by addition of ammonia, is applied on hair wound around rollers (diameter of the rollers: 9 mm); a plastic cap is put in place; there is a wait of 15 minutes; the cap is removed and rinsing is carried out with water; a fixing composition is applied (oxidation) as described in Example 4; it is left to act for 5 minutes; the rollers are removed and, finally, the hair is once again rinsed with water.

Thus, there is finally obtained a lock No. 8 in which the level of keratocysteic acid is equal to 5.3% by weight, that is to say a level which is much greater than that of Example 7.

EXAMPLE 9

Invention

The procedure is carried out as in Example 1, except for this difference: in this instance, the order of implementation between the last rinsing stage and the stage of removal of the rollers is reversed (rinsing then removal).

As in Example 1, hair having good curliness is yet again obtained.

EXAMPLE 10

Invention

The procedure is carried out as in Example 9, except for this difference: the waiting phase of 15 min (Stage (iv) of the process according to the invention) is carried out under an infrared heat dispenser which maintains the hair at a mean temperature of the order of 45° C.

As in Example 1, hair having good curliness is obtained.

EXAMPLE 11

Invention

The procedure is carried out as in Example 10, except for these differences:

the first waiting phase (just after application of the reducing composition) is carried out for 20 min under the heat dispenser, and the second waiting phase (just after the first rinsing) is carried out for 10 min under the dispenser.

As in Example 1, hair having good curliness is obtained.

EXAMPLE 12

Invention

The procedure is carried out as in Example 11, except for these differences: the first exposure time is 10 min and the second exposure time is 20 min.

As in Example 1, hair having good curliness is obtained.

EXAMPLE 13

Invention

This example has the aim of illustrating the invention within the context of a process of "hair setting" type but nevertheless leading to permanent-waved hair.

The procedure in this instance is the following: 1) hair which has been washed beforehand and is still damp is wound around hollow rollers (20 mm in diameter) which are sufficiently airy to allow air to pass from the inside to the outside of the rollers, 2) the composition given in Example 1 is applied on the wound hair (100 ml of lotion per 100 g of hair), 3) a plastic cap is placed on the hair, 4) the combination is placed under an infrared heat dispenser (45° C.), 5) it is left exposed, under the heat dispenser, for 15 min, 6) the dispenser and then the cap are removed, 7) rinsing is carried out with water, 8) the combination is placed under a hot air dispenser (50° C.), 9) the combination is left exposed until the hair is completely dry, 10) the rollers are removed, 11) the hair is brushed in order to set it.

Dry and very resilient hair is finally obtained. After washing with water, the hair has good curliness.

EXAMPLE 14

Invention

The procedure is carried out as in Example 10, but this time using the following composition:

| | |
|---|---|
| cysteine | 7 g |
| monoethanolamine | q.s. pH 9.7 |
| demineralized water | q.s. 100 g |

Hair having good curliness is finally obtained.

EXAMPLE 15

Invention

The procedure is carried out as in Example 10, but this time using the following composition:

| | |
|---|---|
| cysteamine hydrochloride | 11 g |
| monoethanolamine | q.s. pH 9 |
| demineralized water | q.s. 100 g |

Hair having good curliness is finally obtained.

I claim:

1. A treatment process for the permanent deformation of keratinous matter, consisting essentially of the steps of:
   (i) applying to said keratinous matter a composition containing at least one compound selected from cysteine, a cosmetically acceptable salt of cysteine, cysteamine, and a cosmetically acceptable salt of cysteamine, wherein
   said composition has a pH ranging from 9 to 10 when said composition contains cysteine or a cosmetically acceptable salt thereof,
   said composition has a pH ranging from 8 to 9 when said composition contains cysteamine or a cosmetically acceptable salt thereof, and
   said composition has a pH ranging from 8 to 10 when said composition contains both cysteine or a cosmetically acceptable salt thereof and cysteamine or a cosmetically acceptable salt thereof; and further wherein
   said keratinous matter is placed under mechanical tension before, during or after said composition is applied to said keratinous matter;
   (ii) treating said keratinous matter to which said composition has been applied at a temperature ranging from 30 to 60° C.;
   (iii) rinsing said treated keratinous matter;
   (iv) allowing said rinsed keratinous matter to undergo a resting phase for a time period ranging from 10 to 60 minutes; and
   (v) after said resting phase, removing said mechanical tension from said keratinous matter, said keratinous matter having been permanently deformed.

2. A process according to claim 1, wherein said cysteine and cysteamine cosmetically acceptable salts are selected, alone or as a mixture, from hydrochlorides, hydrobromides, citrates, acetates and sulphates.

3. A process according to claim 1, wherein said at least one compound is present in said composition in an amount ranging from 1 to 30% by weight.

4. A process according to claim 3, wherein said at least one compound is present in said composition in an amount ranging from 5 to 20% by weight.

5. A process according to claim 1, wherein said composition further contains at least one cosmetically acceptable adjuvant.

6. A process according to claim 5, wherein said at least one cosmetically acceptable adjuvant is selected from nonionic, anionic, cationic and amphoteric surface-active agents; treatment agents; active ingredients; agents which act against hair loss; anti-dandruff agents; thickening agents; suspension agents; sequestering agents; opacifying agents; dyes; sunscreens; fragrances; and preserving agents.

7. A process according to claim 1, wherein said composition is in the form of a lotion, a cream, or a gel.

8. A process according to claim 1, wherein said keratinous matter is made wet before the application of said composition to said keratinous matter.

9. A process according to claim 1, wherein before carrying out the rinsing operation of step (iii), the keratinous matter treated in accord with step (i) is allowed to rest in a waiting phase, wherein said heat treatment of step (ii) occurs during said waiting phase.

10. A process according to claim 9, wherein said waiting phase lasts for a period ranging from 2 minutes to 30 minutes.

11. A process according to claim 10, wherein said waiting phase lasts for a period ranging from 5 minutes to 20 minutes.

12. A process according to claim 1, wherein heating occurs during the resting phase of stage (iv).

13. A process according to claim 1, wherein said resting phase of stage (iv) lasts for a period ranging from 15 minutes to 30 minutes.

14. A process according to claim 1, wherein said resting phase of stage (iv) is carried out until the rinsed keratinous matter is dry.

15. A process according to claim 1, wherein an additional rinsing operation is carried out following step (iv) or step (v).

16. A process according to claim 15, wherein an additional rinsing operation is carried out following step (v).

17. A process according to claim 1, wherein said keratinous matter is hair.

* * * * *